United States Patent
Tsapatsis et al.

(10) Patent No.: US 9,120,680 B2
(45) Date of Patent: Sep. 1, 2015

(54) MOLECULAR SIEVE MEMBRANES AND THERMAL TREATMENT METHODS OF MAKING THE SAME

(76) Inventors: Michael Tsapatsis, Edina, MN (US); Hae-Kwon Jeong, College Station, TX (US); Jungkyu Choi, Seoul (KR)

( * ) Notice: Subject to any disclaimer, the term of this patent is extended or adjusted under 35 U.S.C. 154(b) by 579 days.

(21) Appl. No.: 13/318,160

(22) PCT Filed: Apr. 30, 2010

(86) PCT No.: PCT/US2010/033133
§ 371 (c)(1),
(2), (4) Date: Feb. 27, 2012

(87) PCT Pub. No.: WO2010/129411
PCT Pub. Date: Nov. 11, 2010

(65) Prior Publication Data
US 2012/0148828 A1  Jun. 14, 2012

Related U.S. Application Data

(60) Provisional application No. 61/176,547, filed on May 8, 2009.

(51) Int. Cl.
| | |
|---|---|
| *B01J 29/06* | (2006.01) |
| *C01B 39/40* | (2006.01) |
| *B01J 29/40* | (2006.01) |
| *B01D 67/00* | (2006.01) |
| *B01D 71/02* | (2006.01) |
| *C01B 39/02* | (2006.01) |
| *C07C 7/13* | (2006.01) |
| *B01J 37/08* | (2006.01) |
| *B01J 35/06* | (2006.01) |

(52) U.S. Cl.
CPC ............ *C01B 39/40* (2013.01); *B01D 67/0051* (2013.01); *B01D 67/0083* (2013.01); *B01D 71/028* (2013.01); *B01J 29/40* (2013.01); *C01B 39/026* (2013.01); *C07C 7/13* (2013.01); *B01D 2323/08* (2013.01); *B01J 35/065* (2013.01); *B01J 37/08* (2013.01); *B01J 2229/10* (2013.01); *B01J 2229/40* (2013.01); *Y10T 428/24999* (2015.04)

(58) Field of Classification Search
USPC .......................... 502/4, 60, 77; 423/700, 709
See application file for complete search history.

(56) References Cited

U.S. PATENT DOCUMENTS

| | | | |
|---|---|---|---|
| 4,581,214 A | 4/1986 | Young | |
| 4,623,633 A * | 11/1986 | Young | ............... 502/85 |
| 5,011,591 A * | 4/1991 | Kuznicki | ......... 208/46 |
| 5,348,924 A | 9/1994 | Potter et al. | |
| 5,824,617 A * | 10/1998 | Lai | ..................... 502/4 |
| 6,136,740 A | 10/2000 | Jones et al. | |
| 7,524,788 B2 | 4/2009 | Girotti et al. | |
| 2007/0137485 A1* | 6/2007 | Bitterlich et al. | ................. 96/11 |
| 2008/0015402 A1 | 1/2008 | Martens et al. | |
| 2009/0000475 A1* | 1/2009 | Fekety et al. | .................... 95/105 |
| 2009/0200236 A1* | 8/2009 | Diefenbacher et al. | ........ 210/640 |

OTHER PUBLICATIONS

Tsapatsis et al."Hierarchical Nanomanufacturing: From Shaped Zeolite Nanoparticles to High-Performance Separation Membranes", Angew. Chem. Int. Ed. 2007, 46, pp. 7560-7573.

* cited by examiner

*Primary Examiner* — Elizabeth Wood
(74) *Attorney, Agent, or Firm* — Fish & Richardson P.C.

(57) ABSTRACT

A thermal processing method for polycrystalline porous films is disclosed. The method and the resulting firms including zeolite films are claimed.

16 Claims, 9 Drawing Sheets

US 9,120,680 B2

MOLECULAR SIEVE MEMBRANES AND THERMAL TREATMENT METHODS OF MAKING THE SAME

This application is the National Stage of International Application PCT/US2010/033133, filed on Apr. 30, 2010, which claims priority to U.S. Provisional Patent Application 61/176,547, filed on May 8, 2009. The contents of the above applications are herein incorporated by reference in their entirety.

TECHNICAL FIELD

This invention relates to molecular sieves, and more particularly to thermal processing of molecular sieves.

BACKGROUND

Zeolites are crystalline oxides with micropores (e.g., pores with sizes in the range of 0.3 to 1.2 nm) and compositions (e.g., Si, Al, Ti, P, Ge, Zn content) that may be fine-tuned for many important applications such as catalysis, adsorption, and ion exchange.

Apart from the use of zeolites in a powder form, thin films and membranes of zeolites are of particular commercial interest as energy-efficient alternatives to current separation and purification processes like distillation, crystallization, and others.

Zeolite molecular sieve membranes can in principle be used in a wide range of operating conditions including high temperatures, high pressures, and in reactive environments, while they can be regenerated for fowling and contamination by aggressive treatments like high temperature calcination under, for example, vacuum or in oxygen or air atmospheres.

Due to these superior properties of zeolite membranes, there have been a range of zeolites prepared in the form of membranes, such as zeolite A, faujasite (X and Y forms), mordenite, ferrierite, MEL, zeolite P, chabazite, SAPO-34, DDR, MFI, i.e., Zeolite Socony Mobil (ZSM)-5.

Thin films of zeolites are technologically valuable for such applications as gas or liquid separations, chemical sensors, membrane reactors, and optoelectronic devices. Due to their well-defined rigid pores in the molecular dimensions and high thermal and chemical stability, zeolite thin films are of particular interests as high resolution selective membranes.

Despite the promise of zeolite membranes as a class of high-performance material, there exist few reports on the practical applications of such membranes. In fact, there is only one commercial application of zeolite membranes so far, zeolite A membranes for water-alcohol separation. To find more commercial applications of zeolite membranes, there are a number of challenges that are yet to be addressed. Some of the challenges include: (1) synthesis of membranes with high permeability and selectivity, which require these membranes to possess small effective thicknesses, and low defect density; (2) membrane fabrication that is cost-effective, reproducible and amenable to scale-up. There is continuing interest to improve the membrane preparation methods and the produced membrane performance.

SUMMARY

Zeolites and other molecular sieve powders and films are often synthesized in the presence of organic structure directing agents, which are occluded in the pores. Before use, these structure directing agents are removed from the pores, usually by high temperature calcination.

Moreover, the pore space of certain molecular sieve powders and films is activated by calcination before they are used for the first time and/or periodically after storage and during operation to remove adsorbed water, organic molecules and other adsorbates. Also, in certain cases, dehydration by calcination results in crystal structure changes like the relocation of extra-framework cations that modify the pore space and separation and/or catalytic performance. For example, the pore size of the titanosilicate zeolite ETS-4 (Engelhard Titanosilicate-4) can be controlled with sub-nanometer resolution by dehydration at different temperatures (the higher the dehydration temperature the smaller the pore) allowing the progressive effective exclusion of smaller molecules [Kuznicki et al. (1999) 33 pp, Kuznicki et al. (2001) Nature 412, 720-724, Kuznicki and Bell (2003) U.S. Pat. No. 6,517,611].

Calcination of powders and, especially, of films is invariably performed with slow heating rates (of the order of few degrees per minute).

We performed, for the first time, calcination of zeolites using very fast heating in a lamp-based Rapid Thermal Processing (RTP) furnace. One advantage is that fast heating results in energy savings. It also allows for faster processing during fabrication of powders and films. Moreover, a major advantage of the new RTP calcination method is that it enables production of molecular sieve materials with distinct structures and, in some cases, with improved performance characteristics that cannot be achieved by conventional calcination.

Of particular interest is the elimination or drastic reduction of grain boundary defects when the first heat treatment step after hydrothermal growth of zeolite films is RTP. The RTP treated zeolite films show remarkably improved separation performance compared with that exhibited by their conventionally calcined counterparts.

The thermal processing method and some of the resulting microstructures will be claimed.

The details of one or more embodiments of the invention are set forth in the accompanying drawings and the description below. Other features, objects, and advantages of the invention will be apparent from the description and drawings, and from the claims.

DETAILED DESCRIPTION

1. General Description of the Methods

Figure 1:
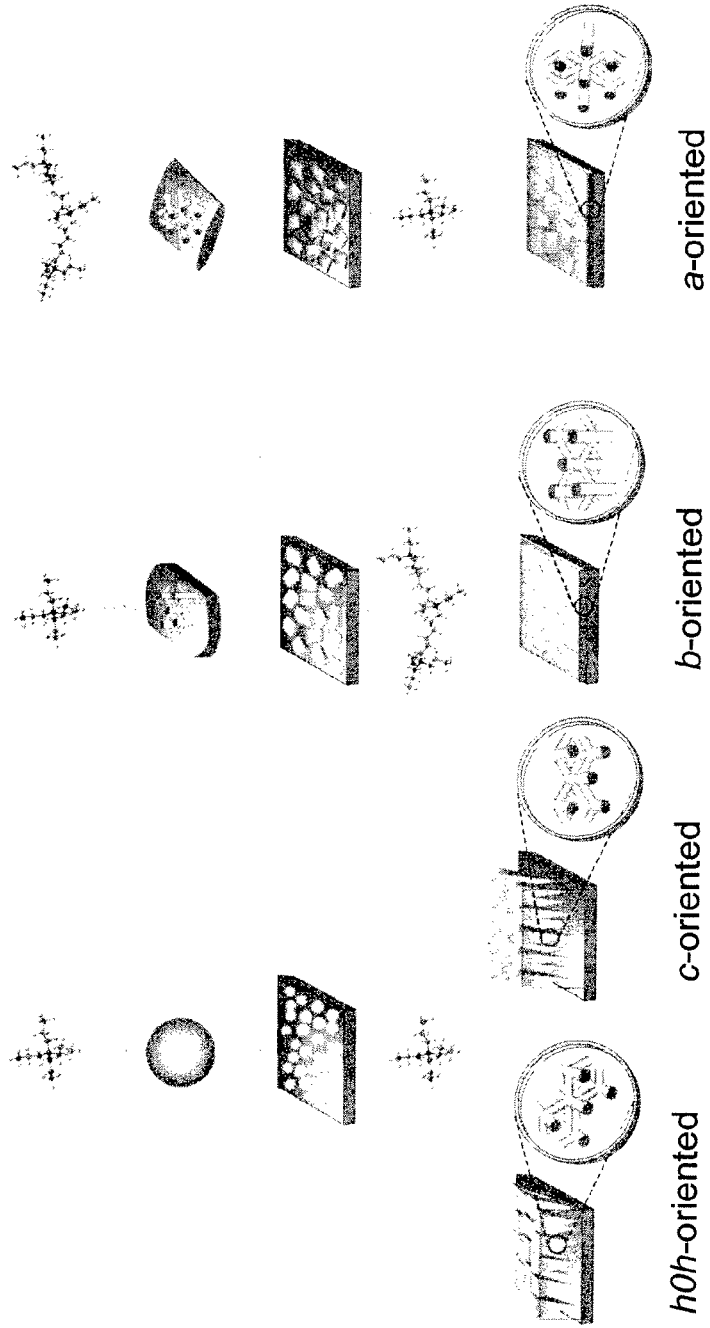
FIG. 1. Schematic of example zeolite film microstructures prepared by growth of seed layers and for which the RTP method can be applied with beneficial effects on performance.

Polycrystalline zeolite films [Davis (2002) Nature 417, 813-821, Lin et al. (2002) Sep. Purif. Methods 31, 229-379, Snyder and Tsapatsis (2007) Angew. Chem., Int. Ed. 46, 7560-7573, Caro and Noack (2008) Micropor. Mesopor. Mater. 115, 215-233] find use as membranes for alcohol dehydration, [Kondo et al. (1997) J. Membr. Sci. 133, 133-141] while other separation, [Yuan et al. (2004) J. Am. Chem. Soc. 126, 4776-4777, Carreon et al. (2008) J. Am. Chem. Soc. 130, 5412-5413] membrane reactor, [Coronas and Santamaria (2004) Top. Catal. 29, 29-44, Dalmon et al. (2007) Appl. Catal., A 325, 198-204] and advanced applications (e.g., sensors, corrosion protection coatings, low-k dielectrics, hosts for guest molecules) have been proposed [Bein (1996) Chem. Mater. 8, 1636-1653, Mintova and Bein (2001) Micropor. Mesopor. Mater. 50, 159-166, Lee et al. (2006) Angew. Chem., Int. Ed. 45, 5288-92, Li et al. (2006) Angew. Chem., Int. Ed. 45, 6329-32, Cai et al. (2008) Angew. Chem., Int. Ed. 47, 525-8, Calzaferri et al. (2008) Chem. Eur. J. 14, 7442-7449].

A major problem preventing development of zeolite film technologies is the formation of thermal-treatment-induced cracks and/or grain boundary defects [Dong et al. (2000) Micropor. Mesopor. Mater. 34, 241-253, Bonilla et al. (2001) J. Membr. Sci. 182, 103-109, Xomeritakis et al. (2001) Ind. Eng. Chem. Res. 40, 544-552] which, for example, are known to drastically affect the separation performance of molecular sieve membranes by providing non-zeolitic and, often, non-selective transport pathways for permeating species.

Successful approaches to reduce grain boundary and crack effects rely on film growth processes that allow microstructure optimization [Hedlund et al. (2002) Micropor. Mesopor. Mater. 52, 179-189, Lai et al. (2003) Science 300, 456-460, Carreon et al. (2008) J. Am. Chem. Soc. 130, 5412-5413] and development of defect reparation techniques [Nomura et al. (1997) Ind. Eng. Chem. Res. 36, 4217-4223, Yan et al. (1997) J. Membr. Sci. 123, 95-103, Xomeritakis et al. (2001) Ind. Eng. Chem. Res. 40, 544-552]. However, they require multi-step fabrication processes that hinder cost-effective and reliable scale-up.

A determining factor in microstructure development is the first heat treatment step after hydrothermal film growth to remove structure directing agents (SDA) and/or other guest species occluded in the zeolite pores during crystal growth. Invariably, this calcination step is performed at very low heating (typically 1-5° C./min) rates in an attempt to minimize crack and other extra-zeolitic defect formation.

Surprisingly, we discovered that very fast calcination using a conventional furnace or preferably using a lamp-based Rapid Thermal Processing (RTP) furnace can drastically reduce grain boundary and other defects (like, for example, transverse cracks propagating across the entire film thickness) and result in membranes with significantly improved separation performance. The improvement is more pronounced when lamp-based RTP treatment is used.

We also discovered that zeolite powders and films can be calcined effectively, i.e., remove all SDA from the pores, using RTP treatment only. RTP treatment is a faster (by a factor of up to approximately 500) and more energy efficient (by a factor of up to approximately 50) process compared to conventional calcination.

Conventional calcination is typically performed at heating rates of the order of 1-5° C./min and by keeping the zeolite powder and film isothermal at a temperature typically between 200 and 500° C. for several hours, e.g. 5 hours. RTP heating takes place at rates in excess of 100° C./min, typically 500° C./min or more. The zeolite sample (powder or film) is then be kept isothermally at a temperature higher than 300° C. and up to 700° C. or up to 800° C. for few minutes, e.g., 1 min, and then cooled down to room temperature within few minutes, e.g., 1 min. The fast heating and short isothermal treatment result in substantial energy savings (simple estimates suggest 50-fold reduction in energy requirements).

Moreover, from the production standpoint RTP allows fast processing and high throughput capability. This can be very important in large scale continuous production of zeolites. It can be especially important in large scale production of zeolite coatings and films for membrane and other applications. A simple calculation indicates that energy required for RTP treatment (infrared chamber and water cooler from Research Inc.) is about 50 times less than that for conventional calcination (Thermolyne 48000 series). Assuming that 1 day and 5 min (plus 30 min cooling by water circulation) are required for conventional calcination and RTP treatment, respectively, 1800 watt×(3600×24) sec/day×1 day (=1.5×10$^5$ kJ) is required for the former, while 4800 watt×5×60 sec+1000 watt×60×30 sec (=3.2×10$^3$ kJ) for the latter.

RTP can be performed using commercially available industrial infrared heaters such as infrared heaters from Research Inc (www.researchinc.com). The chambers could have different shapes (i.e., cylinders and boxes) to match the size and shape of the supports used. The heaters could be closed (for batch operation) or open (for continuous operation).

RTP can be applied to as synthesized zeolite powders, binder free or binder containing zeolite pellets, zeolite coated monoliths (e.g., silicon carbide, alumina), zeolite films and membranes on flat supports (e.g., silicon wafers, flat porous alumina supports, flat stainless steel and aluminium supports, flat porous stainless steel supports with and without coating like titania, zirconia, silica and others).

RTP can also be applied to dehydration of zeolite powders with beneficial effects including the preservation of the crystallinity and high pore volume of the zeolite framework.

RTP can also be applied during the preparation of metal and other cluster containing zeolites to control the cluster size and location of metal and other particles.

For the case of supported films, RTP furnace geometry and size should be selected considering the geometry of the support used, i.e., to conform with the shape and size of the substrates used to support the zeolite films. For example, for zeolite films supported on tubular supports a tubular furnace should be selected while for films supported on flat supports like silicon wafers a box furnace should be selected.

RTP can be performed under vacuum, atmospheric or elevated pressure; it can be performed with or without flow of inert, reducing (e.g., hydrogen) or oxidizing (e.g., water, oxygen or air) gases; also, several RTP steps can be combined in series in order to optimize performance (e.g., membrane selectivity), crystal structure and microstructure. Moreover, RTP can be combined with conventional calcination; for example an RTP calcination can be followed by one or more conventional calcination steps.

2. General Description of the Materials Formed Using the Methods

We demonstrated that SDA removal from zeolite powders can be completely or partially accomplished using RTP. RTP can also be used to prepare dehydrated zeolites and to thermally treat ion exchanged or metal or cluster impregnated zeolites. By use of RTP, we prepare materials that can be substantially similar to or substantially different from those prepared by conventional calcination.

After a certain sequence of RTP, or RTP and conventional calcination, treatments the X-Ray Diffraction (XRD) pattern and pore volume (as determined by nitrogen adsorption at liquid nitrogen temperature) obtained are indistinguishable from that of conventionally calcined powders and films.

After certain other sequences of RTP treatments, for example using a single RTP treatment, the XRD pattern and adsorption capacity are different from the ones obtained from the conventionally calcined samples. In some cases these differences reveal partial blocking of the pores. Pore blocking, although in most cases is undesirable, in some cases can be beneficial; for example when one wants to effectively exclude molecules with sizes smaller than the zeolite pore size from entering the zeolite pores [Niwa et al. (1986) J. Phys. Chem. 90, 6233-7, Zidek et al. (1997) Pet. Coal 39, 29-31, Weber et al. (1998) Micropor. Mesopor. Mater. 23, 179-187, Chen et al. (2002) J. Mol. Catal. A: Chem. 181, 41-55].

RTP can be used for the thermal treatment of a zeolite film supported on a substrate.

Zeolite films are different from zeolite powders because they consist of intergrown grains and contain grain boundaries. Grain boundaries are created when zeolite grains merge with other ones in a zeolite film. The importance of grain boundaries in the performance of zeolite films is well recognized in many publications as described in a recent review [Caro and Noack (2008) Micropor. Mesopor. Mater. 115, 215-233]. For example, if grain boundaries are weakly connected they can open up during heat treatment or operation creating pores larger than the zeolite pores which can have detrimental effects in, for example, membrane performance by providing non selective transport pathways.

We discovered that distinct film microstructures can be prepared by use one or more RTP thermal treatments. Some of these microstructures have drastically improved performance in important applications. For example, they are highly selective membranes while membranes without RTP treatment (but otherwise identically prepared) show no or very small selectivity.

Without being limited by any theory, we attribute these improvements to the strengthening of the grain boundary bonding by the RTP treatment enhancing condensation, dehydration and dehydroxylation reactions at the grain boundaries. Improved grain boundary bonding is demonstrated by use of dye experiments and confocal microscopy that are described below and in the Examples.

RTP treatment can also introduce new microstructural characteristics that are not observed without RTP treatment. In one case lateral disk-shape delaminations are created during RTP. The presence of these delaminations has never been observed before in zeolite films. In zeolite membranes it is correlated with improved separation performance.

Without being limited by any theory we attribute these lateral disk-shape delamination defect structures to local stress concentration developed during RTP treatment that results from disparate (due to the rapid heating) removal rates of molecules occluded in the pores or their decomposition products from the film interior in comparison to regions nearer the membrane surface. Concomitant mismatch in the extent of unit cell contraction between empty and pore-filled regions could conceivably be relieved by film buckling and manifested as discoid delaminations.

The RTP treatment can be applied to all known zeolite structures and compositions in the form of powders and films. For a compilation of zeolite structures see the Atlas of Zeolite Structures [Baerlocher et al. (2007)].

To demonstrate the beneficial effects of RTP we used one of the many available zeolites and one of the many available film microstructures. However, the method is general and applicable to all zeolite materials and film microstructures.

A typical zeolite that is used in industry is ZSM-5 (MFI framework; see [Baerlocher et al. (2007)]) which is synthesized using as structure directing agent (SDA) tetrapropylammonium ions which are occluded in the zeolite pores. Films of this zeolite have been extensively studied. FIG. 1 shows schematics of representative ZSM-5 film microstructures that can be achieved using secondary growth of seed layers. The methods for synthesis of these films are described in a recent review and references therein [Snyder and Tsapatsis (2007) Angew. Chem., Int. Ed. 46, 7560-7573]. RTP treatment can be applied to all of these membranes.

To demonstrate the effect of RTP treatment we used thick columnar c-out-of-plane preferentially oriented films of siliceous ZSM-5 ($[Si_{96}O_{192}]$-MFI [Flanigen et al. (1978) Nature 271, 512-16]) prepared by secondary growth of randomly oriented seeds [Gouzinis and Tsapatsis (1998) Chem. Mater. 10, 2497-2504, Xomeritakis et al. (1999) Chem. Eng. Sci. 54, 3521-3531] for the reasons explained in the next paragraph.

The growth mechanism and separation performance of these films have been studied extensively. Their synthesis procedure is simpler, easier to reproduce and apply to various substrates, and more amenable to scale up by comparison to other zeolite membrane syntheses [O'Brien-Abraham et al. (2007) Micropor. Mesopor. Mater. 105, 140-148]. However, the presence of transverse grain boundary defects produced during conventional (slow rate) calcination for SDA removal is well documented for these membranes and correlated with poor separation performance. [Dong et al. (2000) Micropor. Mesopor. Mater. 34, 241-253, Xomeritakis et al. (2001) Ind. Eng. Chem. Res. 40, 544-552, Gu et al. (2006) J. Membr. Sci. 280, 624-633, Lassinantti Gualtieri et al. (2007) J. Membr. Sci. 290, 95-104, O'Brien-Abraham et al. (2007) Micropor. Mesopor. Mater. 105, 140-148, Caro and Noack (2008) Micropor. Mesopor. Mater. 115, 215-233] These grain boundary defects are formed in response to tensile stresses caused mainly by the abrupt zeolite unit cell contraction upon SDA removal as well as the thermal expansion coefficient mismatch between the substrate and the zeolite film [Dong et al. (2000) Micropor. Mesopor. Mater. 34, 241-253, Jeong et al. (2005) Micropor. Mesopor. Mater. 84, 332-337]. Depending on membrane operating conditions (temperature, pressure, mixture composition), the extra-zeolitic pore openings at the grain boundaries may become substantially larger than the zeolite pores and compromise membrane performance [Xomeritakis et al. (2001) Ind. Eng. Chem. Res. 40, 544-552]. For example, the presence of grain boundary defects has been associated with the poor performance of c-oriented columnar membranes for xylene isomers (p- vs. o-xylene) and the reduction of the mixture separation factor for butane isomers at elevated temperatures. In particular, despite the high single component ideal selectivity (up to ~100), for xylene isomers, the separation factor for the corresponding binary mixture is less than 4 [Xomeritakis et al. (2000) Micropor. Mesopor. Mater. 38, 61-73].

We decided to explore RTP as the first heat treatment step after hydrothermal growth hoping to reduce the formation of grain boundary defects. Although we are not limited by any theoretical interpretation of our findings, we hypothesized that the very fast arrival to a high temperature could give rise to Si—OH group condensation reactions—which enhance grain bonding at the grain boundaries—before the onset of in-plane tensile stresses caused by the SDA removal. A possible and desirable outcome of this strengthening of the grain boundary bonding before tensile stress development could be a reduced flexibility and pore-opening of the grain boundaries.

Indeed, we found a beneficial effect of the RTP step on membrane performance for otherwise similarly prepared c-oriented MFI membranes. We observed a remarkable improvement in the separation of xylene isomers, with mixture p-/o-xylene separation factor reaching up to 128 from values lower than 3. Moreover, the butane and hexane isomer mixture separation factor at the higher end of the investigated temperature range is also consistently improved for the RTP treated membranes. The combination of high selectivity for both xylenes (up to 128) and butanes (up to 34) has not been achieved before with a single MFI membrane microstructure. For example, the b-oriented MFI membranes that hold the record for xylene separation (mixture separation factor up to 480) show very small butane selectivity (up to 6) [Lai et al. (2003) Science 300, 456-460, Lai and Tsapatsis (2004) Ind. Eng. Chem. Res. 43, 3000-3007].

Figure 2:
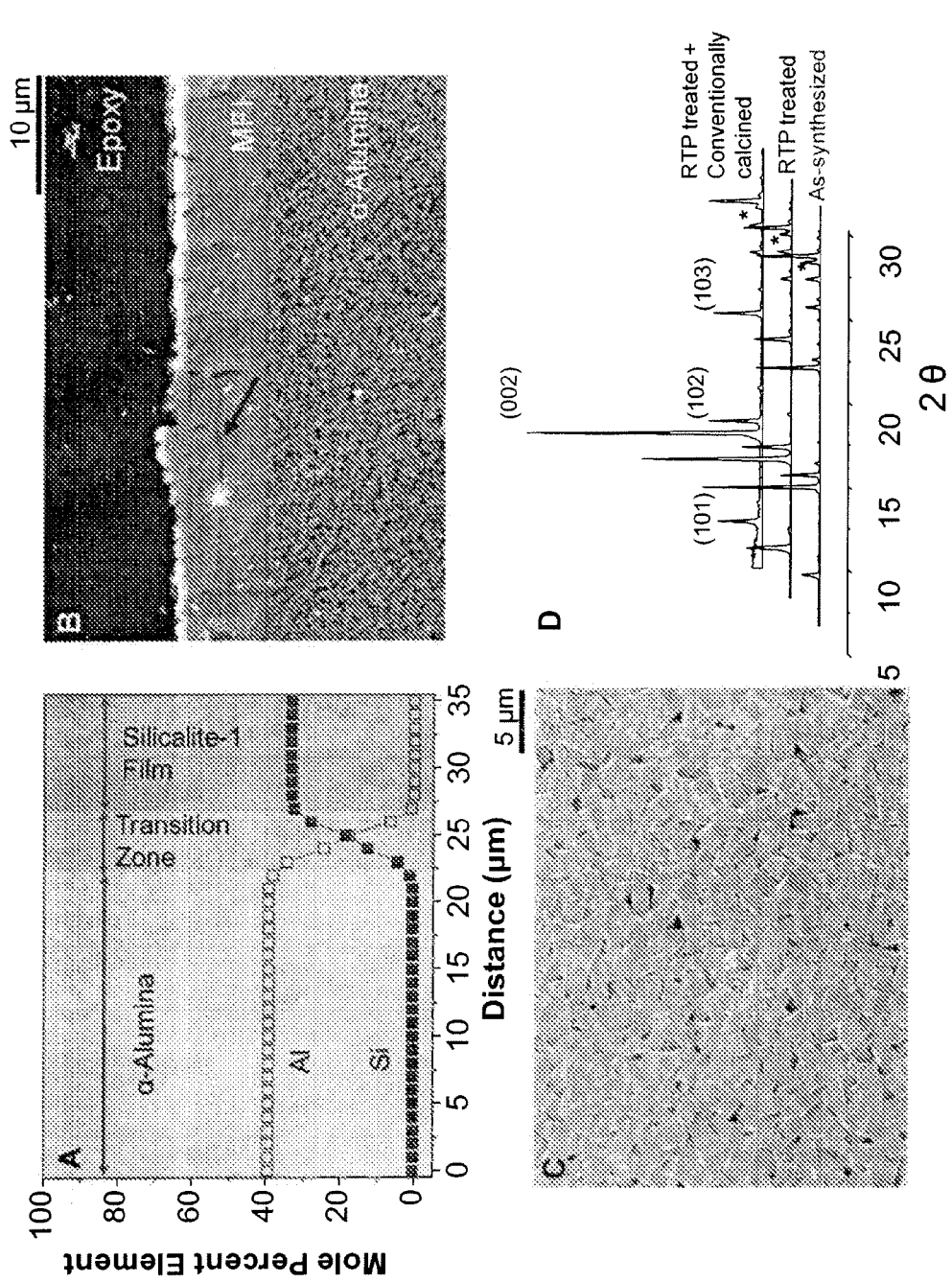
FIG. 2. EPMA trace (A) of composition across the membrane thickness and SEM cross section (B) of RTP treated and then conventionally calcined membrane. A lateral delamination is marked by an arrow. The top view SEM is shown in (C), and the corresponding XRD traces are shown in (D). For the elemental analysis, the cross section was probed for Si and Al along the membrane thickness in steps of 1 µm starting from the α-alumina substrate and using wavelength-dispersive spectrometers in a JEOL JXA-8900. The SEM image in (B) was collected after cross sectioning (with a diamond saw), embedding in epoxy, polishing and sputter coating calcined membranes with gold for observation with a scanning electron microscope. The XRD data were collected using a Bruker-AXS (Siemens) D5005 diffractometer operating with $\lambda$ (CuK$\alpha$)=1.5406 Å. The XRD patterns in (D) were normalized by the porous α-alumina support peak designated by asterisk (*) in order to see the relative intensity differences at each stage: as-synthesized, RTP treated, and RTP treated with additional conventional calcination.

Electron Probe Micro-Analysis (EPMA), Scanning Electron Microscopy (SEM), and X-Ray Diffraction (XRD) (FIG. 2) do not reveal any difference between the conventionally calcined and RTP treated MFI membranes with the exception of the presence of 10-100 μm lateral delaminations present approximately in the middle of the thickness of RTP treated membranes. Fluorescent Confocal Optical Microscopy (see discussion below and FIG. 3) confirms the presence and location of these delaminations and reveals that they have a disk shape. A possible cause for their formation may be the slower removal of the SDA from the interior parts of the film causing stresses due to different extends of unit cell contraction that are relieved by the film buckling at the observed discoid delaminations. That some SDA or SDA decomposition products remain in the RTP treated films while they are completely removed by a following conventional calcination is suggested by the relative intensity of the XRD peaks. See, for example, the relative (002) reflection intensity increase, signifying SDA removal, [Lassinantti Gualtieri et al. (2007) J. Membr. Sci. 290, 95-104] after RTP followed by further increase after the additional calcinations (FIG. 2D). It is further supported by permeation and adsorption data as discussed below.

Figure 3:
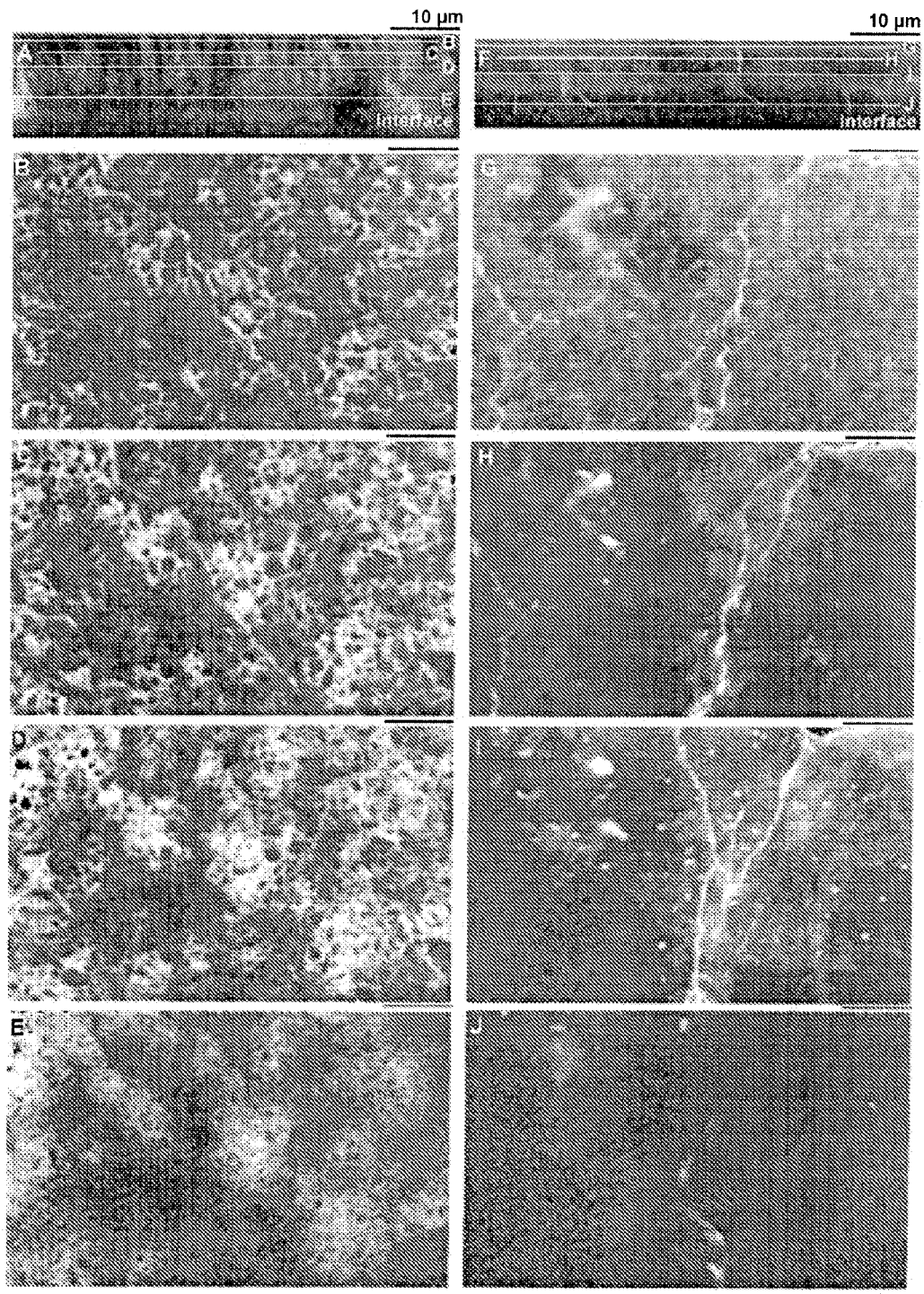
FIG. 3. Fluorescence Confocal Optical Microscopy (FCOM) cross sections of conventionally calcined (0.5° C./min) (A), and RTP treated (700° C./min) and then conventionally calcined (0.5° C./min) (F), c-oriented MFI membranes along with the corresponding slices taken approximately at 2 μm (B, G), 6 μM (C, H), 10 μm (D, I), and 18 μm (E, J) from the surface as indicated by horizontal lines in (B) and (F), respectively. Lateral delaminations, observed approximately in the middle of the RTP treated and then conventionally calcined c-oriented MFI film, are marked by blue arrows in (F). A discoid delamination is partially observed in (I).
Figure 4:
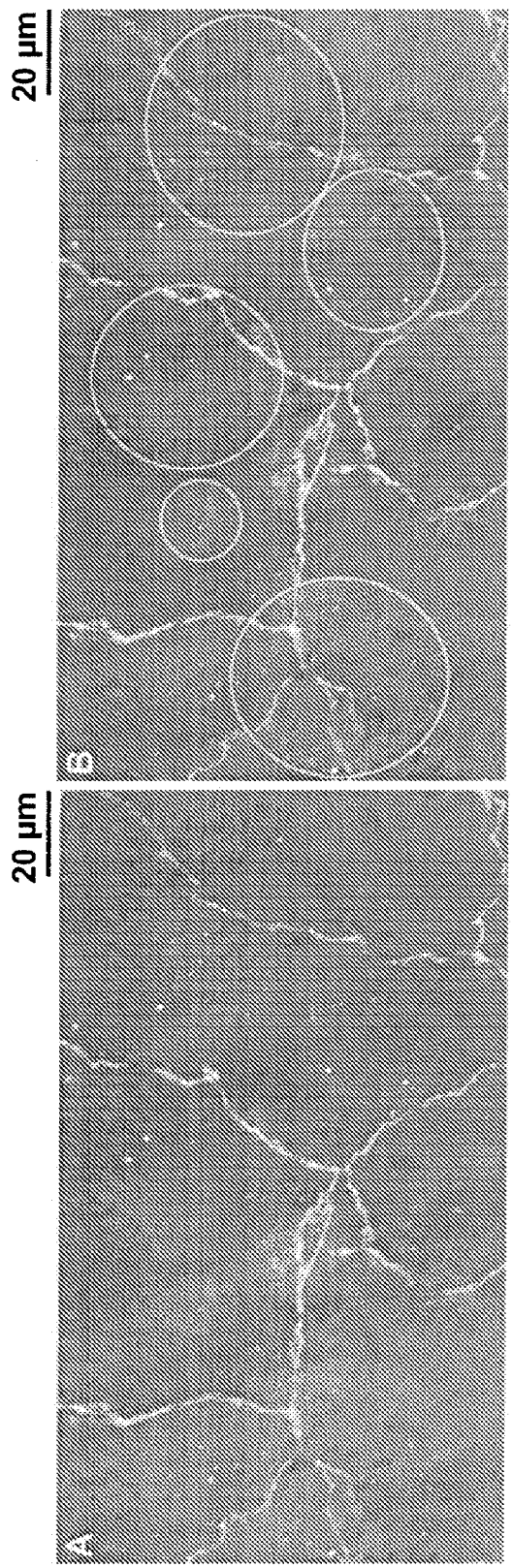
FIG. 4. (A) Fluorescence optical slice of a RTP treated and then conventionally calcined c-oriented MFI membrane taken at approximately 7 μm below the surface showing lateral discoid delaminations some of which are highlighted by circles or ellipses in (B) for ease of recognition.

Without being limited by any theory, we attribute the improved permeation performance to elimination of grain boundary defects. FIG. 3 shows representative results from the examination of conventionally and RTP treated membranes using Fluorescent Confocal Optical Microscopy (FCOM). The images were taken after contacting the membranes for 48 h with a solution of a fluorescent dye (Fluorescein-Na salt) that is larger (estimated size of ~1 nm) than, and therefore, unable to enter in the zeolite pores (about 0.6 nm in size) [Bonilla et al. (2001) J. Membr. Sci. 182, 103-109]. Conventionally calcined columnar membranes have been examined before by FCOM [Bonilla et al. (2001) J. Membr. Sci. 182, 103-109, Snyder et al. (2004) Micropor. Mesopor. Mater. 76, 29-33]. It was shown that the fluorescent dye can be readily detected highlighting with bright fluorescence the grain boundaries across the membrane thickness indicating the presence of extra-zeolitic transport pathways with pore openings that are or can become (upon dye adsorption) larger than the zeolite pores. The conventionally calcined membranes prepared in this study show, as expected, the above mentioned typical and well established behavior. In contrast, the RTP treated, but otherwise similarly prepared films, show only sporadic penetration of the fluorescent dye across the membrane thickness indicating less flexible and/or smaller openings at the grain boundaries, a finding that correlates with their improved separation performance. FCOM also reveals the presence of a large number of lateral discoidal delaminations described in the previous paragraph and shown by SEM in FIG. 2B and FCOM in FIG. 4. The delaminations are not likely to compromise the separation performance since they do not span the transverse direction of the zeolite membrane. Although a cause-and-effect relation between the lateral discoid delaminations and the reduction of transverse grain boundary defects in RTP treated membranes cannot be established, both are consistent with our initial hypothesis regarding strengthening of grain bonding at the grain boundaries before SDA removal.

We have also explored the possibility of performing calcination exclusively by RTP as a possible replacement for the time consuming and energy intensive conventional calcination steps (i.e., with a faster (by a factor of 500) and more energy efficient (by a factor of 50) one). After a single RTP step, however, the permeances of the faster permeating species (e.g., n-butane) were measured to be an order of magnitude lower than those obtained after an additional calcination step, indicating that some SDA and/or SDA decomposition products remain in the zeolite pores following RTP treatment. This remnant SDA is most likely a result of mass transport limitations on the rate of SDA release during the rapid (i.e., 1 minute) RTP treatment.

That a single RTP step is not sufficient to completely open the micropores is underscored by the XRD data discussed above (FIG. 2D). Although a calcination step after RTP seems to be necessary to completely open the micropores, results indicate that this second calcination can be performed by RTP without need for conventional calcinations. The concomitant savings in both time and energy that could be realized by replacing conventional calcination by two RTP treatments hold exciting implications for pushing zeolite membrane synthesis closer to broader commercial realization.

3. Possible Applications for the Materials

The materials produced by including RTP treatment can be used in conventional (e.g., adsorption, catalysis, ion exchange) and novel or emerging (e.g., molecular sieve membranes, thin insulating films, catalytic coatings on monoliths) applications of zeolites. For example, the resulting high selectivity membranes can be used for the separation and purification of petrochemical streams like aromatic isomers and linear vs. branched hydrocarbons; and the purification of biorefinery process streams like ethanol dehydration, and separation of sugars from their dehydration products.

4. Examples

Example 1

Demonstration that RTP Treatment has a Beneficial Effect in Membrane Separation Performance: Comparison of Two Otherwise Identically Treated Membranes with One Being Also Treated by RTP after Hydrothermal Synthesis. (Actual)

c-Oriented MFI membranes were synthesized by secondary (or seeded) growth according to well established procedures available in the open literature. A brief description of the synthesis process is as follows. Home-made α-alumina support discs were made by pressing α-alumina power and sintering them. One side of each disc was polished by a sand paper and was further coated with a thin mesoporous layer. Randomly oriented seed layers were formed via a chemical bonding through a silane agent (3-chlororpropltrimethoxysilane) between ~100 nm sized globular MFI particles and silica-coated surface following a so-called sonication-assisted method [Lee et al. (2005) Adv. Mater. 17, 837-841]. The seeded support was calcined at 450° C. for 4 h with 1° C./min ramp rate under 150 cc/min air flow. After that, the seed layer on the support was subsequently hydrothermally intergrown to a 15~20μ thick c-oriented MFI film. The molar composition of solution for hydrothermal growth was 40 tetraethoxy orthosilicate (TEOS, Aldrich): 9 tetrapropylammonium hydroxide (TPAOH, Aldrich): 9500 DI water: 160 Ethanol. This methodology in membrane fabrication is known as secondary (or seeded) growth. Detailed information of how to prepare α-alumina disc, silica sol, and seed crystals and perform silica coating, seed layer formation, and secondary growth can be found elsewhere [Choi et al. (2006) Adsorption 12, 339-360].

The membranes made by the procedure described above were then separated in two sets of three. Triplicate experiments were performed in which three membranes were conventionally calcined in a calcination furnace using a slow calcination ramp rate; and three other identically grown membranes were first treated by RTP and then calcined in a calcination furnace using a slow calcination ramp rate. Conventional calcinations were done by heating membranes up to 480° C. with 0.5° C./min ramp rate, holding that temperature for several hours (usually 10~12 h), and slowly cooling them down to room temperature (Thermolyne 48000 series). For RTP treatment, a lamp-based furnace was used to heat up as-synthesized membranes up to 700° C. within a minute, soak at that temperature for 30 sec, while the membranes were cooled down by water circulation. An infrared chamber (E4-10 from Research Inc.) was used and controlled by a Eurotherm temperature controller (Model 2404)) and a water to air heat exchanger (C100-1 from Research Inc.) was used to cool down the furnace.

Figure 5:
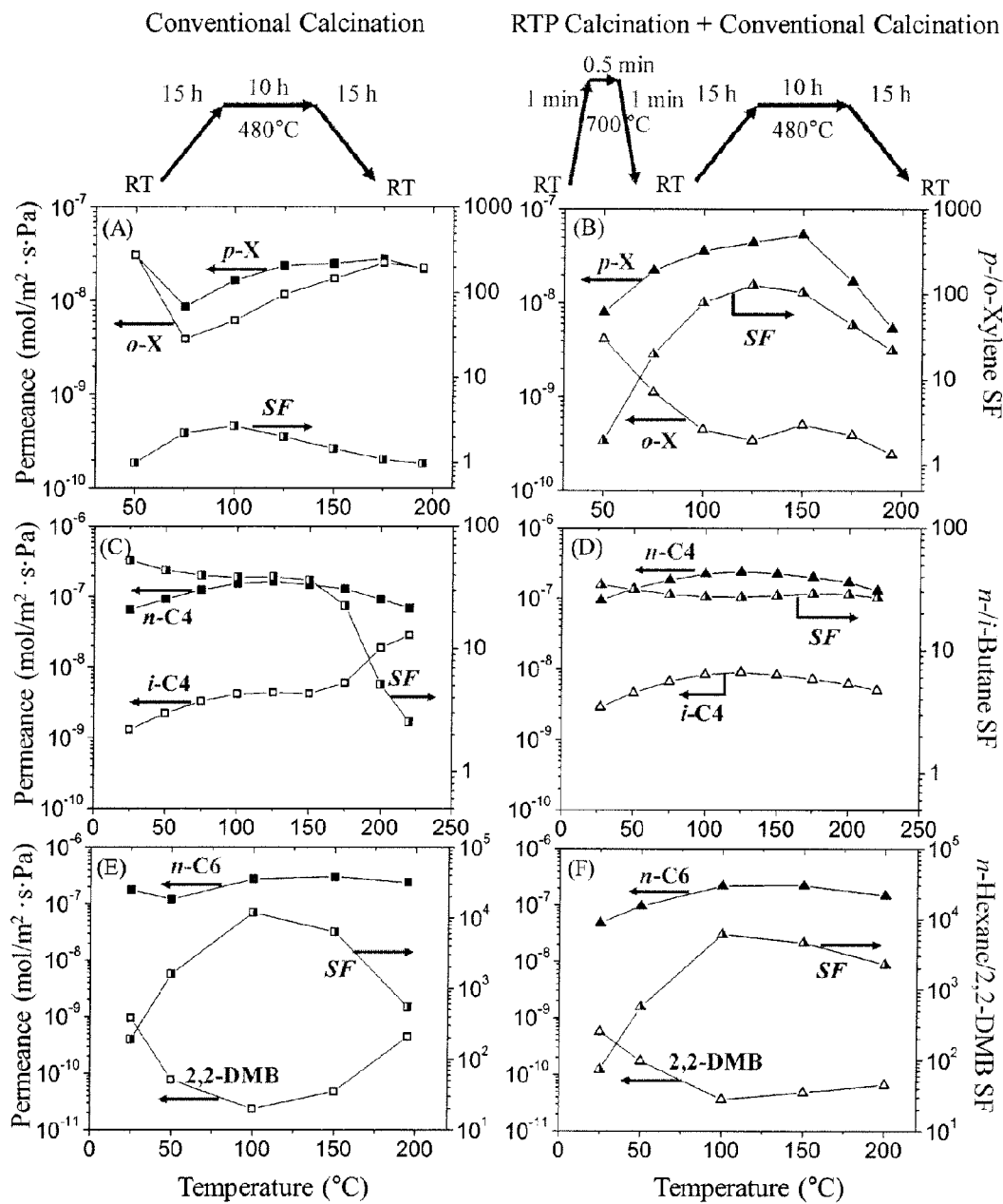
FIG. 5. Xylene (A, B), butane (C, D), and hexane (E, F) separation performance of conventionally calcined (0.5° C./min) (A, C, E), and RTP treated (700° C./min) and then conventionally calcined (0.5° C./min) (B, D, F) c-oriented MFI membranes. The compositions of the feed mixtures were: 0.50 KPa/0.50 KPa for p-xylene/o-xylene; 50 KPa/50 KPa for n-butane/i-butane; and 13 KPa/13 KPa for n-hexane/2,2-dimethylbutane (2,2-DMB).

FIG. 5 shows the xylene (p- and o-xylene), butane (n- and i-butane), hexane (n-hexane and 2,2-dimethylbutane) mixture separation performance (i.e., permeances and the corresponding separation factor (SF)) of one of the conventionally calcined and one of the RTP treated (and then further conventionally calcined) c-oriented MFI membranes. Permeance is defined as flux through the membrane divided by pressure gradient across the membrane, while separation factor (SF) is defined as $$SF = \frac{y_{permeate}/x_{permeate}}{y_{feed}/x_{feed}}$$

where $y_{feed}$ and $x_{feed}$ are mole fractions of y and x in feed side, respectively, and $y_{permeate}$ and $x_{permeate}$ are mole fractions of y and x in permeate side, respectively with y being the faster permeating component (n-butane, n-hexane, or p-xylene). The permeation measurements for separation performance were done in Wicke-Kallenbach mode and the triplicate experiments are within 20% of the values given in this example. The detailed permeation set-up was described in Ref. [Choi et al. (2006) Adsorption 12, 339-360]. It is clear that a RTP treatment resulted in dramatic improvement in membrane performance. This example also demonstrated that RTP treatment can be combined with conventional calcination. The distinct microstructure of the RTP treated films was characterized and is described in Example 8.

Example 2

Demonstration that RTP Treatment can Lead to Partial Opening of the Zeolite Pores. (Actual)

A single RTP treatment of an as-synthesized c-oriented MFI membrane (made as described in Example 1) was performed as follows: a membrane was heated to 700~800° C. within one minute, held for 30 sec, and cooled by water circulation.

Figure 6:
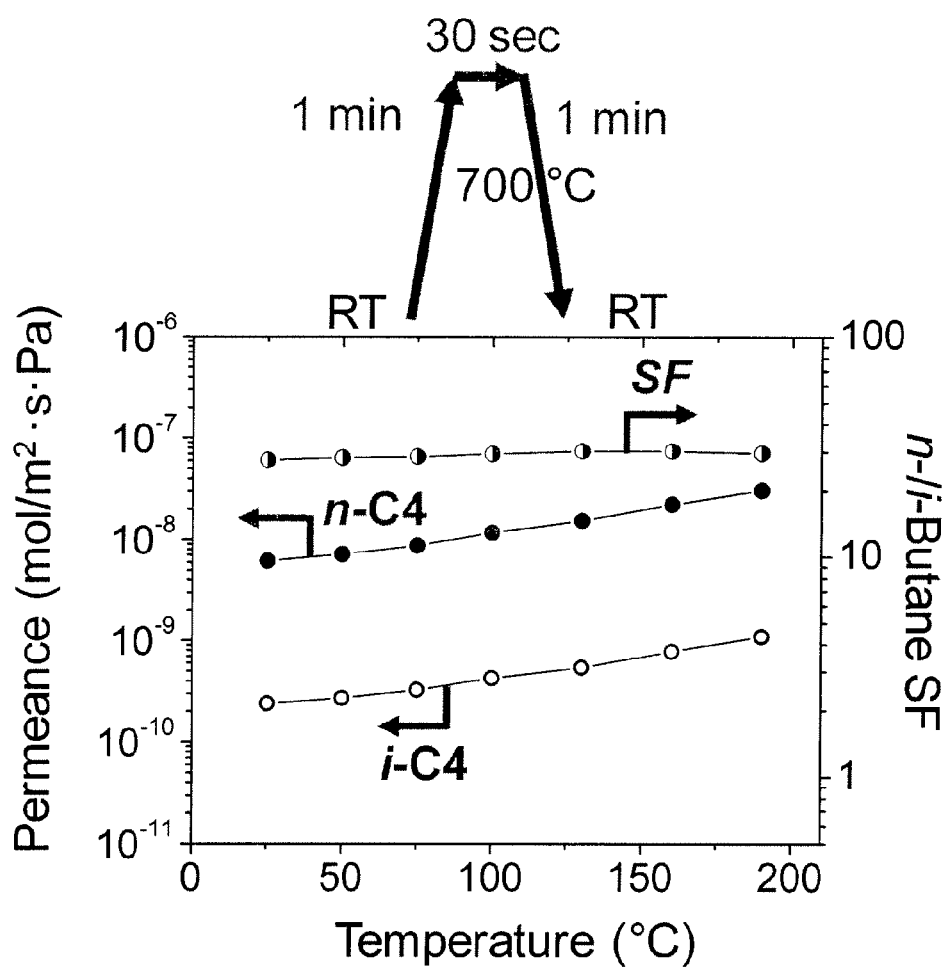
FIG. 6. Butane binary mixture (n- and i-butane) permeances and the corresponding separation factor through an only RTP treated c-oriented WI membrane made on an α-alumina disc.

Permeances of both n- and i-butane isomers (FIG. 6) were about one order of magnitude lower than those through a conventionally calcined (compared with permeances given in FIGS. 5C and 5D). This indicated that the RTP treatment performed as described above was not sufficient to remove structure directing agents (SDAs) completely. Moreover, that some SDA or SDA decomposition products remain in the RTP treated films described in the current example is suggested by the relative XRD peak intensities. For example, the intensity of the XRD peak corresponding to the (002) plane after RTP was increased as compared to the corresponding one in an as-synthesized film, but was still lower than the intensity of the corresponding peak obtained after RTP and additional conventional calcination (FIG. 2D). For appropriate comparison, all the XRD peaks were normalized by the peak from the α-alumina support. This example demonstrated that RTP treatment can be used to partially open pores in zeolite films.

Example 3

Demonstration that RTP Treatment Alone can Completely Open the Zeolite Pores While Still Having the Beneficial Effects in Performance. (Actual)

c-Oriented as-synthesized MFI films were made by secondary growth as described in Example 1. Two sequential RTP treatments were performed by (1) heating membranes to 700° C. with 700° C./min ramp rate, holding 700° C. for 2 min, then cooling to room temperature and (2) heating again membranes to 700° C. with 700° C./min ramp rate and holding 700° C. for 1 min, and then cooling to room temperature. The same set up used in Example 1 was adopted here for RTP treatment.

Figure 7:
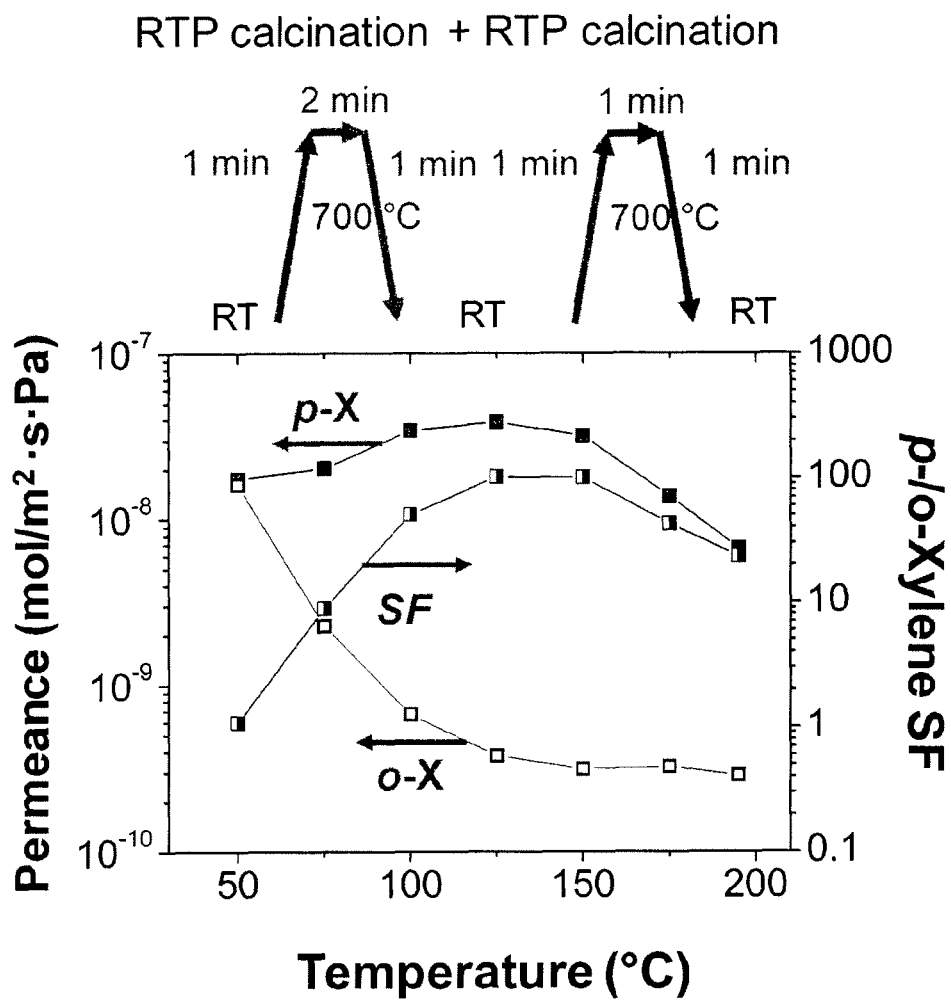
FIG. 7. Xylene separation performance of an only two-time RTP treated (700° C./min) c-oriented MFI membrane. The composition of the feed mixtures was 0.50 KPa/0.50 KPa for p-xylene/o-xylene.

FIG. 7 shows that the xylene mixture separation performance of this RTP treated MFI membrane was also dramatically improved as compared to a conventionally calcined MFI membrane and that the performance is almost identical to that of the RTP treated and further conventionally calcined MFI membrane shown in Example 1.

This example demonstrated that pores of zeolite films can be opened by RTP treatment alone. Taking into account the total 1~2 d usually required for conventional calcinations, RTP treatments held promise in time saving (calcination can be achieved in 10 min or less) and also reduced energy consumption. This makes RTP very attractive for commercial large scale zeolite film and zeolite membranes, in particular, production.

Example 4

Demonstration that RTP Treatment on MFI Type Zeolite Powder can Partially Remove Occluded Structure Directing Agents (SDAs) Present Inside Zeolite without Damage. (Prophetic)

MFI type zeolite crystals are synthesized from the clear solution that is obtained by hydrolyzing TEOS in TPAOH/water medium. RTP treatment is carried out on the MFI zeolite powder following a similar temperature profile and using the same RTP experimental set up as described in Example 1: MFI powder is heated to 700° C. with 700° C./min ramp rate, held at that temperature for 30 sec, and cooled down by water circulation.

Scanning Electron Microscopy (SEM) images do not reveal any distinct features between as-synthesized MFI powder and conventionally calcined MFI power. It is well established in the open literature that the unique, characteristic X-Ray Diffraction (XRD) patterns before and after conventional calcinations (i.e., before and after pore opening) distinguish between a XRD pattern of as-synthesized MFI power from that of conventionally calcined MFI power. Therefore, XRD characterization of RTP treated MFI powder is used as an indicator of whether it is successfully calcined. A XRD pattern of RTP treated MFI power, if it is similar to that of conventionally calcined powder, indicates pore openings inside MFI powder by exposing MFI powder to a RTP treatment (on the order of 1 min). The similarity between the XRD patterns of RTP treated and conventionally calcined powders also reflects the preservation of the crystallinity of MFI zeolite. XRD patterns, however, do not inform how much of pores in MFI powder is opened by RTP treatment so, additionally, thermogravimetric analysis (TGA) and $N_2$ adsorption isotherms are further performed for quantitative analysis. Results from both experiments indicate that a short time exposure of a zeolite membrane to RTP treatment removes SDAs partially, consistent with the incomplete calcination of a RTP-treated c-oriented MFI membrane shown in Example 2. An additional conventional calcination to RTP treatment on MFI zeolite particles is necessary in order to remove the remaining SDAs. Nonetheless, optimization of operating conditions during RTP treatment on as-synthesized MFI power has potential to complete zeolite pore openings after just one time RTP treatment.

Example 5

Demonstration that Two Time RTP Treatments on MFI Type Zeolite Powder can Lead to the Complete Opening of Zeolite Pores. (Prophetic)

MFI type zeolite is synthesized as described in Example 4. Two RTP treatments on MFI zeolite are performed consecutively, following a similar temperature profile and using the same RTP experimental set up as described in Example 1: MFI powder is heated to 700° C. with 700° C./min ramp rate, held at that temperature for 30 sec, and cooled down by water circulation and RTP treatment is repeated one more time.

SEM characterization detects no difference between as-synthesized MFI powder and two time RTP treated MFI powder. In addition, the XRD pattern after one time RTP treatment is indicative of remaining pore material, while the additional RTP treatment leads the XRD pattern to be almost identical to that of conventionally calcined MFI powder. This reflects the complete opening of zeolite pores after two time RTP treatments that are considered as equivalent to conventional calcination in removing occluded SDAs. The complete pore opening is further supported by quantitative analysis techniques: thermogravimetric analysis (TGA) and $N_2$ adsorption isotherms. These characterizations show almost identical results to those from conventionally calcined MFI powder.

The complete pore opening by two time RTP treatments without any difference from conventionally calcined MFI powder is consistent with Example 3 in which a two time RTP treated MFI membrane shows almost an identical permeation behavior to that of a RTP treated and further conventionally calcined MFI membrane.

Example 6

Demonstration that RTP Treatment can have Similar Beneficial Effect on Zeolite Films Supported on Different Support (E.G., Tubular Porous Stainless Steel) (Actual)

Secondary growth was further extended to fabricate c-oriented MFI membranes on top of porous stainless steel tubes (purchased from Pall Corp. and cleaned by acetone). At first, dried ~0.05 g of globular MFI crystals (~100 nm in diameter) were placed in a home-made glass reactor (consists of two parts: a bottom and top part allowing the insertion of a support and liquid surrounding the support and allowing for flow of gases to control the atmosphere above the liquid) and ~110 ml anhydrous toluene was added to it. The glass reactor, immersed in a water bath, was further sonicated for ~30 min to disperse MFI crystals. Right after that, a stainless steel tube was vertically placed in the glass reactor and an additional sonication (10~20 min) was applied to deposit those MFI crystals on to the stainless steel support. During the whole procedure for seed deposition, non-humid environment was maintained by using Ar flow. A seeded support was calcined at 450° C. for 4 h with 1° C./min ram rate. After that, the clear solution, prepared by hydrolyzing TEOS in TPAOH/water medium, was filtered into a Teflon-liner where a seeded tube was already positioned vertically. The molar composition of the solution was 40 or 60 $SiO_2$: 9 TPAOH: 9500 $H_2O$: 160 or 240 EtOH.

The same classification for calcination as the way given in Example 1 was applied to as-synthesized c-oriented MFI films made on stainless steel tubes: one was conventionally calcined in a furnace (Thermolyne 48000 series), while the other was RTP treated and further conventionally calcined. Conventional calcinations were done by heating membranes up to 480° C. with 0.5° C./min ramp rate, holding that temperature for several hours (usually 10~12 h), and slowly cooling them down to room temperature. For RTP treatment, a lamp-based furnace was used to heat up as-synthesized membranes up to 700° C. within a minute, soak at that temperature for 30 sec, while the membranes were cooled down by water circulation. An infrared chamber (E4-10 from Research Inc.) was used and controlled by a Eurotherm temperature controller (Model 2404)) and a water to air heat exchanger (C100-1 from Research Inc.) was used to cool down the furnace.

Figure 8:
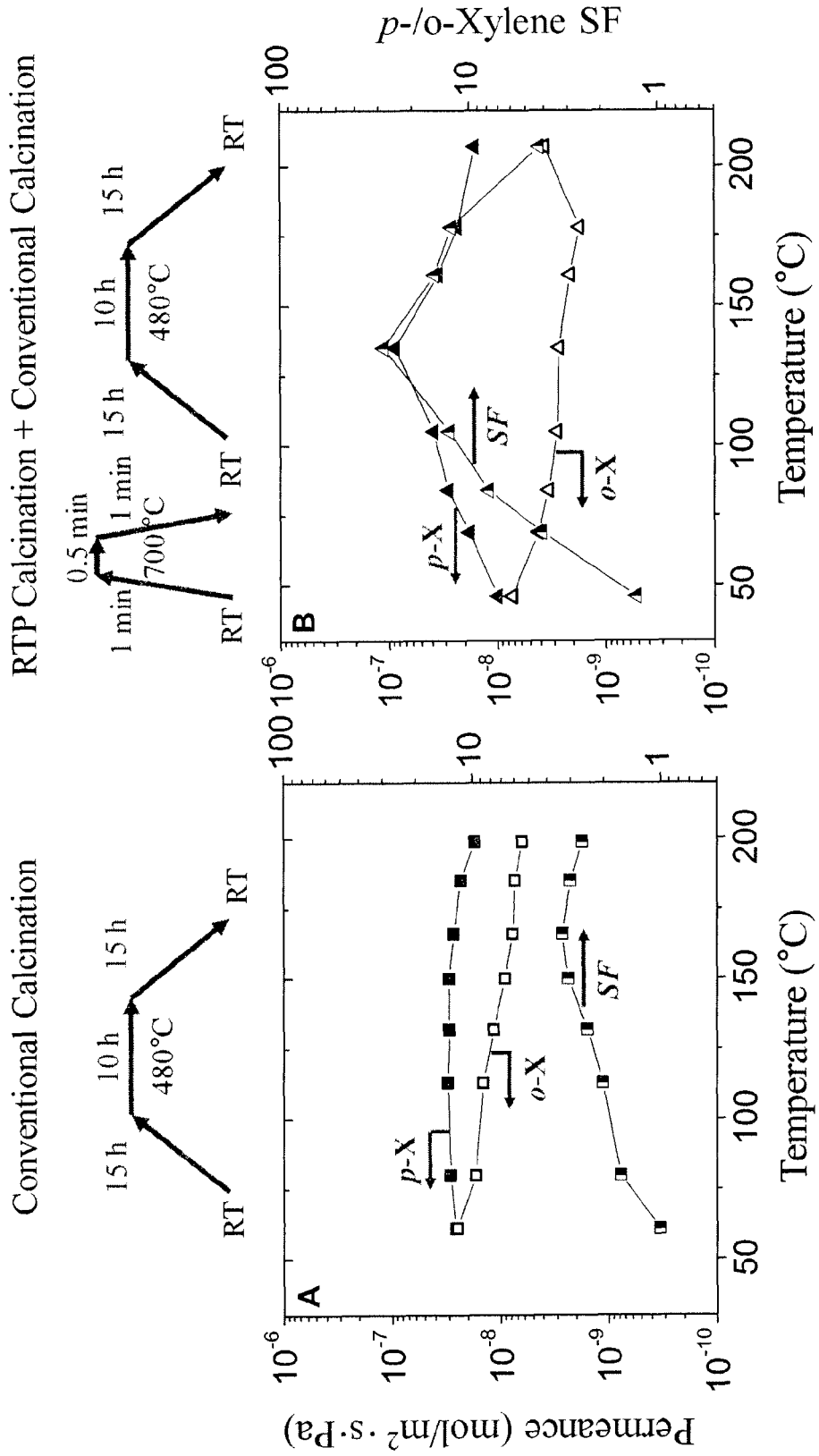
FIG. 8. Xylene separation performance of conventionally calcined (0.5° C./min) (A), and RTP treated (700'C/min) and then conventionally calcined (0.5° C./min) (B), c-oriented MFI membranes. The composition of the feed mixtures was 0.50 KPa/0.50 KPa for p-xylene/o-xylene. The set up for permeation measurements was based on Wicke-Kallenbach mode using a home-made tubular quartz permeation cell.

SEM characterization (using a JEOL 6700 without the application of any coating) showed the typical and expected features, i.e., columnar grains. FIG. 8 shows the separation performance of a RTP-treated and then conventionally calcined membrane (up to 28 p-/o-xylene separation factor) was considerably enhanced as compared to that of a conventionally (with no RTP treatment) calcined membrane (up to 4 p-/o-xylene separation factor). The set up for permeation measurements was based on Wicke-Kallenbach mode using a home-made tubular quartz permeation cell, and otherwise similar equipment and procedures as for the MFI membranes made on α-alumina discs in Example 1.

Example 7

Figure 9:
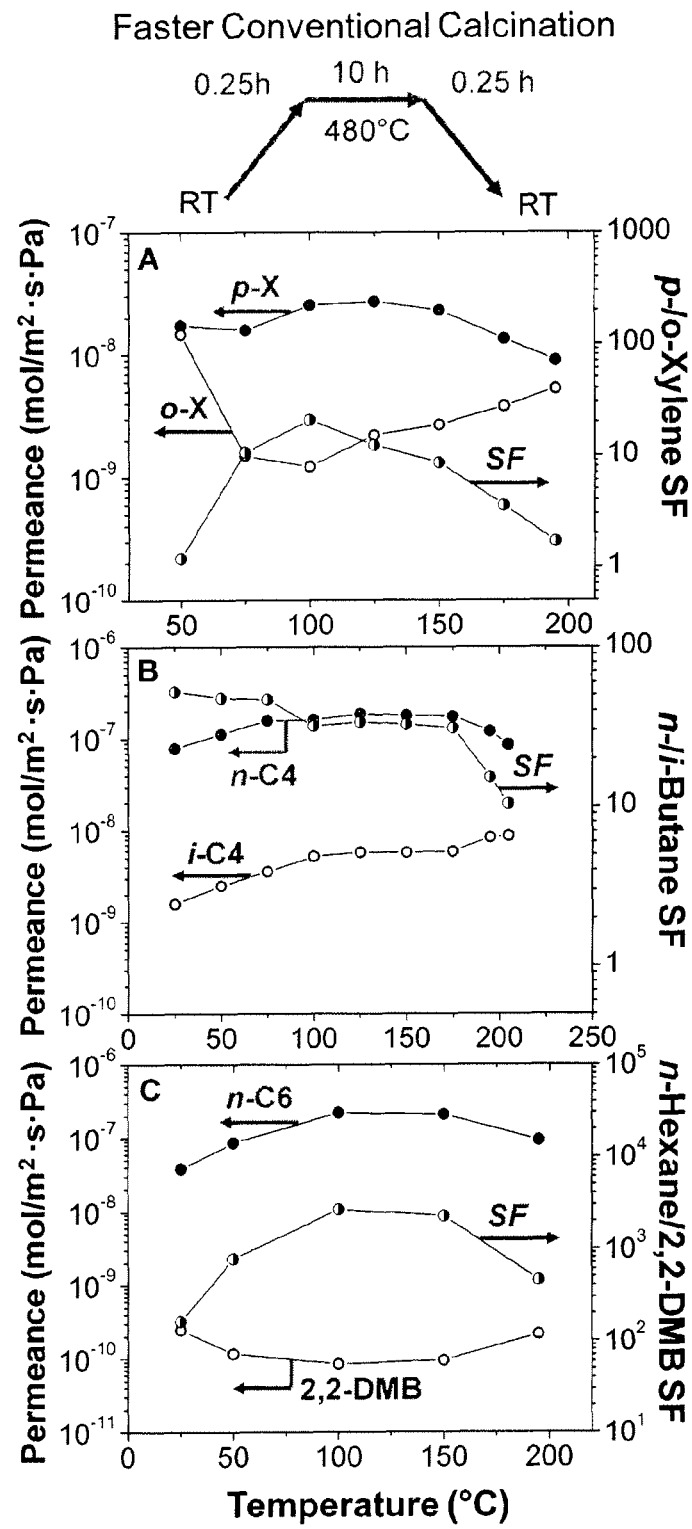
FIG. 9. Xylene (A), butane (B), and hexane (C) separation performance of fast calcined (30° C./min) c-oriented MFI membranes. The compositions of the feed mixtures were: 0.50 KPa/0.50 KPa for p-xylene/o-xylene; 50 KPa/50 KPa for n-butane/i-butane; and 13 KPa/13 KPa for n-hexane/2,2-dimethylbutane (2,2-DMB).

Demonstration that Fast Calcination Ramp Rate can have Beneficial Effects Even in Conventional Furnace (No Lamp Based) but the Effect is Much Less Pronounced. (30° C./Min Ramp Rate) (Actual)

c-Oriented as-synthesized MFI films were made by secondary growth as described in Example 1. The zeolite pores of films were opened by heating samples up to 480° C. with 30° C./min ramp rate, soaking that temperature for 10~12 h, and cooling them slowly. The faster calcination was performed in a conventional furnace (Thermolyne 48000). FIG. 9 shows faster conventional calcinations (30° C./min), albeit less pronounced compared to RTP treatment shown in Example 1, also led to the improvement of separation properties (e.g., up to 20 p-/o-xylene separation factor) as compared to about 3 separation factor through a conventionally calcined membrane as shown in FIG. 5A.

Example 8

Demonstration of Distinct Microstructure Created by RTP: Reduced Grain Boundary Defects and Lateral Delaminations (Actual)

Fluorescence Confocal Optical Microscopy (FCOM) was used to visualize the non-zeolitic (i.e., defects) networks inside zeolites. The membrane side of each sample was contacted with a fluorescent molecular probe dye solution (1 mM Fluorescein-Na salt/DI water solution) for 48 h by using an "osmosis-type" home-made glass cell, while the other side (α-alumina support) was contacted with DI water. FCOM images along the film thickness were taken by a Microscope (Olympus FluoView FV1000 Inverted) and a home-made sample holder. The dye molecules used here (estimated size of 1 nm) were large enough not to penetrate into zeolitic parts (approximately 0.6 nm), while they were small enough to be fully accessible to non-zeolitic parts. Therefore, bright spots represented the presence of dye molecules designating non-zeolitic areas (i.e., defects), while dark spots represented the absence of dye molecules indicating well intergrown zeolitic parts. Grain boundary defects in a conventionally calcined membrane, not detectable for example by a SEM technique, were ubiquitously widespread throughout the surface and propagated along the film thickness toward supports (FIG. 2A-E). The clear features of grain boundary defects were being weakened toward supports but bright spots were still observed near the interface between zeolite films and supports (FIG. 2A). This indicated that grains, grown from globular seed layers, were well intergrown compactly near the interface. As opposed to such a typical microstructure, a RTP treated and further conventionally calcined MFI membrane had distinct feature (FIG. 2F-J). There were no clear grain boundary features, while cracks were easily observed throughout the surface (FIG. 2G). It seems that the cracks did not propagate completely toward supports near the membrane/support interface (FIG. 2F).

At first, the improved separation performance for xylene, butane, and hexane isomer mixtures through RTA treated and further conventionally calcined c-oriented MFI membranes in Example 1 could be attributed to the little to no grain boundary defects on these films, while the density of these grain boundary defects, equally accessible to any species of mixtures, was large enough to ruin any enhancement of separation performance of conventionally calcined c-oriented MFI membranes. Secondly, incomplete crack propagation could be another contributing factor form improved separation. Even, cracks, if any, appearing to fade away near the membrane/support interface, did not look large compared to seemingly large cracks detected in conventionally calcined membranes. More specifically, the compact, defect-free portion of a RTA treated and further conventionally calcined c-oriented MFI membranes especially near the interface between films and supports helped zeolite membranes to play a role of the intrinsic molecular sieve as originally expected.

FCOM also confirmed the presence, location, and lateral orientation (parallel to membrane/support interface) of delaminations, and revealed that they had a disk shape as indicated by arrows in FIG. 2F and highlighted in FIG. 3. These defect structures could be due to local stress concentration developed during RTP treatment that resulted from disparate removal rates of SDA or its decomposition products from the membrane interior in comparison to regions nearer the membrane surface. Concomitant mismatch in the extent of unit cell contraction between empty and SDA-filled regions could conceivably be relieved by film buckling and manifested as discoid delaminations. These were, however, unlikely to compromise the separation performance since they did not span the transverse direction of the zeolite membrane.

Variations. A number of embodiments of the invention have been described. Nevertheless, it will be understood that various modifications may be made without departing from the spirit and scope of the invention. For example:

Higher or lower soaking temperatures can be used (i.e., other than the approximately 700° C. used for the Examples mentioned here). The optimal temperature is expected to vary depending on the zeolite structure type, preferred orientation, grain size and film thickness and support used but can be readily determined by systematic exhaustive investigation of the effect of temperature on performance. Higher or lower ramp rates to the soaking temperature can be used (i.e., other than the approximately 700° C./min used for the Examples mentioned here). The optimal temperature ramp rate is expected to vary depending on the zeolite structure type, preferred orientation, grain size and film thickness and support used but can be readily determined by systematic exhaustive investigation of the effect of temperature ramp rate on performance.

Different combinations of ramp rates and soaking temperatures can be used. For example, a ramp rate of 500, 600, 700, 800, 900, or 1000° C./min to a soaking temperature of 800, 900, or 1000° C.

More combinations of RTP treatments and conventional calcinations can be used for beneficial effects determined by permeation measurements and microscopy imaging.

In the Examples mentioned herein, RTP treatments were performed while maintaining an oxygen atmosphere. Variations may include different flow rates and compositions of the gas phase during RTP treatment for beneficial effects determined by permeation measurements and microscopy imaging.

The rapid thermal processing of polycrystalline films can be achieved by any heating methods that can heat the materials to high temperatures (up to 1000° C. or greater) on a timescale of several seconds or less. Such rapid heating can be attained by high intensity lamps or laser process. The lamps are generally based on infrared (IR) electromagnetic waves. However, the rapid thermal processing can also be achieved using electromagnetic waves having different frequency ranges such as radio frequency (RF), microwaves (MW), visible, and ultraviolet (UV). One can also envision any heating sources other than using electromagnetic waves applicable to the rapid thermal processing of polycrystalline films as long as they are capable of heating materials rapidly to several hundred on a timescale of several seconds or less. For example, any commercial rapid thermal processing equipment used during semiconductor device fabrication processes can be used for the rapid thermal processing of polycrystalline films. There are many manufacturers that make rapid thermal processing (or annealing) systems (to name a few, Koyo Thermo Systems Co. (http://www.crystec.com/kllrtpe.htm), Jipelec (http://www.jipelec.com/), Axic (http://www.axic.com/), Engineering Solutions (http://www.eng-sol.net/), Surface Science Integration (http://www.ssintegration.com/), Allwin21 (http://www.allwin21.com/)). The chambers of the rapid thermal processing systems can be operated under a wide range of pressure (i.e., from vacuum, atmospheric pressure to high pressure) and also be purged with diverse gases such as pure nitrogen, oxygen, argon, helium, and other light gases as well as organic vapors and their mixtures.

Other zeolite or microporous membranes can be treated by the methods described here including all zeolite structure types, metal-organic frameworks and sol-gel silica, titania, zirconia, alumina and other oxide membranes. Optimal combinations of RTP soaking times, ramp rates, gas atmospheres, etc. can be determined by testing for permeation properties and by examination of grain boundaries using optical and electron microscopy.

Accordingly, other embodiments are within the scope of the following claims.

What is claimed is:

1. A method for processing a zeolite film or powder comprising at least one heat treatment step to temperatures larger than 300° C. with heating rates larger than 30° C/min,
   wherein the zeolite film or powder is a non-calcined zeolite film or powder, and
   wherein the zeolite is an MFI-type zeolite.

2. The method of claim 1 comprising at least one heat treatment step to temperatures larger than 300° C. with heating (temperature ramp) rates larger than 400° C/min accomplished in a lamp-based rapid thermal processing furnace.

3. A method for preparing a zeolite film comprising of depositing zeolite seed crystals on a support, further treating the deposited seed crystals by bringing them in contact with a growth medium until they become substantially intergrown and further treating the obtained film using the method of claim 1.

4. A zeolite film processed by the method of claim 1.

5. A zeolite film processed by the method of claim 2.

6. A zeolite film prepared by the method of claim 3.

7. A zeolite film processed by the method of claim 2 with the space between the zeolite crystal grains (grain boundary) being inaccessible to molecules larger than the zeolite pore.

8. A zeolite film prepared by the method of claim 3 with the space between the zeolite crystal grains (grain boundary) being inaccessible to molecules larger than the zeolite pore.

9. A zeolite film processed by the method of claim 2, the zeolite film containing lateral delaminations.

10. The zeolite film of claim 8 further containing lateral delaminations.

11. An article, comprising:
    the zeolite film of claim 10; and
    a porous support supporting the zeolite film.

12. The article of claim 11 where the zeolite film comprises of columnar grains with a c-out-of-plane crystallographic orientation.

13. The article of claim 12, wherein the article has a para-xylene/orto-xylene mixture separation factor larger than 20.

14. The article of claim 13, wherein the article further exhibits a normal-butane/iso-butane mixture separation factor larger than 20 at temperatures larger than 200° C.

15. A method for treating zeolite MFI films, comprising:
    treating a zeolite MFI film with a lamp-based infrared heater at temperatures higher than 300° C.

16. The method of claim 1, wherein the non-calcined zeolite film or powder comprises a structure directing agent.

* * * * *

UNITED STATES PATENT AND TRADEMARK OFFICE
CERTIFICATE OF CORRECTION

PATENT NO.        : 9,120,680 B2
APPLICATION NO.   : 13/318160
DATED             : September 1, 2015
INVENTOR(S)       : Michael Tsapatsis, Hae-Kwon Jeong and Jungkyu Choi It is certified that error appears in the above-identified patent and that said Letters Patent is hereby corrected as shown below:

Claims

Column 16, Claim 13, Line 47:

Delete "xylene/orto-xylene" and Insert -- xylene/ortho-xylene --

Signed and Sealed this
Ninth Day of February, 2016

Michelle K. Lee
*Director of the United States Patent and Trademark Office*